(12) United States Patent
Folan et al.

(10) Patent No.: US 11,406,522 B2
(45) Date of Patent: Aug. 9, 2022

(54) DEPLOYABLE SLEEVES AND RELATED METHODS

(71) Applicant: Boston Scientific Scimed, Inc., Maple Grove, MN (US)

(72) Inventors: Martyn G. Folan, Loughrea (IE); David R. Wulfman, Minneapolis, MN (US); Damien V. Nolan, Galway (IE); Martin Hynes, Galway (IE); Matthew Montague, Galway (IE); Thomas M. Keating, Tuam (IE); Adeniyi O. Aremu, Brooklyn Park, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 559 days.

(21) Appl. No.: 15/806,620

(22) Filed: Nov. 8, 2017

(65) Prior Publication Data
US 2018/0125691 A1 May 10, 2018

Related U.S. Application Data

(60) Provisional application No. 62/419,707, filed on Nov. 9, 2016.

(51) Int. Cl.
*A61M 31/00* (2006.01)
*A61F 2/07* (2013.01)
(Continued)

(52) U.S. Cl.
CPC .............. *A61F 5/0076* (2013.01); *A61F 2/02* (2013.01); *A61F 5/0003* (2013.01); *A61F 5/003* (2013.01);
(Continued)

(58) Field of Classification Search
CPC ........ A61F 5/0076; A61F 2/02; A61F 5/0003; A61F 5/003; A61F 5/004; A61F 5/0036;
(Continued)

(56) References Cited

U.S. PATENT DOCUMENTS 5,439,446 A * 8/1995 Barry ...................... A61F 2/958
604/103.01
6,059,823 A * 5/2000 Holman ........... A61B 17/12045
623/1.15
(Continued)

FOREIGN PATENT DOCUMENTS

WO 93/05730 A1 4/1993
WO 96/14027 A1 5/1996
(Continued)

OTHER PUBLICATIONS

GI Dynamics, "EndoBarrier", <http://gidynamics.com/endobarrier/>, Accessed Nov. 2, 2017, 2 pages.
(Continued)

*Primary Examiner* — Nicholas J. Weiss
*Assistant Examiner* — Alessandro R Del Priore
(74) *Attorney, Agent, or Firm* — Bookoff McAndrews, PLLC

(57) ABSTRACT

A medical device may include a tubular sleeve configured for implantation in a body lumen, the sleeve having a first configuration with a first rigidity and a second configuration with a second rigidity greater than the first rigidity, the sleeve including: a flexible membrane defining an interior lumen; and a channel extending along the membrane.

14 Claims, 3 Drawing Sheets

(51) Int. Cl.
*A61F 2/04* (2013.01)
*A61F 2/88* (2006.01)
*A61F 2/95* (2013.01)
*A61F 5/00* (2006.01)
*A61F 2/02* (2006.01)

(52) U.S. Cl.
CPC ............ *A61F 5/004* (2013.01); *A61F 5/0036* (2013.01); *A61M 31/005* (2013.01); *A61F 2/07* (2013.01); *A61F 2/88* (2013.01); *A61F 2002/044* (2013.01); *A61F 2002/045* (2013.01); *A61F 2002/072* (2013.01); *A61F 2002/9511* (2013.01); *A61F 2230/0091* (2013.01); *A61F 2250/001* (2013.01); *A61F 2250/0003* (2013.01); *A61F 2250/0007* (2013.01); *A61F 2250/0012* (2013.01); *A61F 2250/0018* (2013.01); *A61F 2250/0068* (2013.01); *A61M 2205/0266* (2013.01)

(58) Field of Classification Search
CPC ............ A61F 2/07; A61F 2250/0003; A61F 2002/045; A61F 2002/044; A61F 2250/0068; A61F 2250/001; A61F 2250/0018; A61F 2250/0012; A61F 2/88; A61F 2250/0007; A61F 2002/9511; A61F 2230/0091; A61F 2002/072; A61F 2/94; A61F 2/95; A61F 2/954; A61F 2002/065; A61F 2/89; A61F 2002/075; A61M 31/005; A61M 2205/0266; A61B 17/12045; A61B 17/12118; A61B 2017/00004; A61B 2017/00535; A61B 2017/1205; A61B 2017/12127
See application file for complete search history.

(56) References Cited

U.S. PATENT DOCUMENTS

| | | | |
|---|---|---|---|
| 6,149,681 | A | 11/2000 | Houser et al. |
| 6,395,019 | B2* | 5/2002 | Chobotov ............... A61F 2/07 623/1.13 |
| 7,935,073 | B2 | 5/2011 | Levine et al. |
| 9,173,759 | B2 | 11/2015 | Nelson et al. |
| 2005/0171593 | A1* | 8/2005 | Whirley ............... A61F 2/06 623/1.13 |
| 2010/0016943 | A1* | 1/2010 | Chobotov ............... A61F 2/07 623/1.11 |
| 2011/0082442 | A1* | 4/2011 | Solovay ............... A61M 25/02 604/524 |
| 2015/0088244 | A1* | 3/2015 | Chobotov ............... A61F 2/07 623/1.35 |
| 2016/0095733 | A1 | 4/2016 | Sharma et al. |
| 2018/0049761 | A1* | 2/2018 | Bashir ............... A61B 17/22 |

FOREIGN PATENT DOCUMENTS

WO 2013/087093 A1 6/2013
WO 2013/087096 A1 6/2013

OTHER PUBLICATIONS

E. Tamussino & Cia LTDA, "Esophageal Z-Stent With Dua Anti-Reflux Valve", <http://www.tamussino.com.br/en/produto-det.php?rp=314>, Accessed Nov. 2, 2017, 1 page.

* cited by examiner

FIG. 3A
FIG. 3B
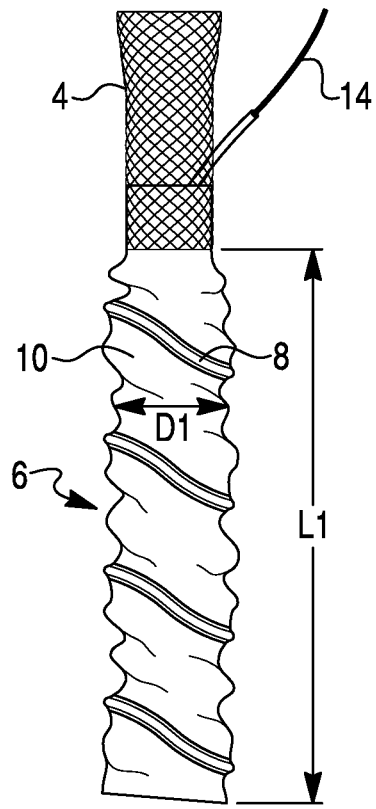
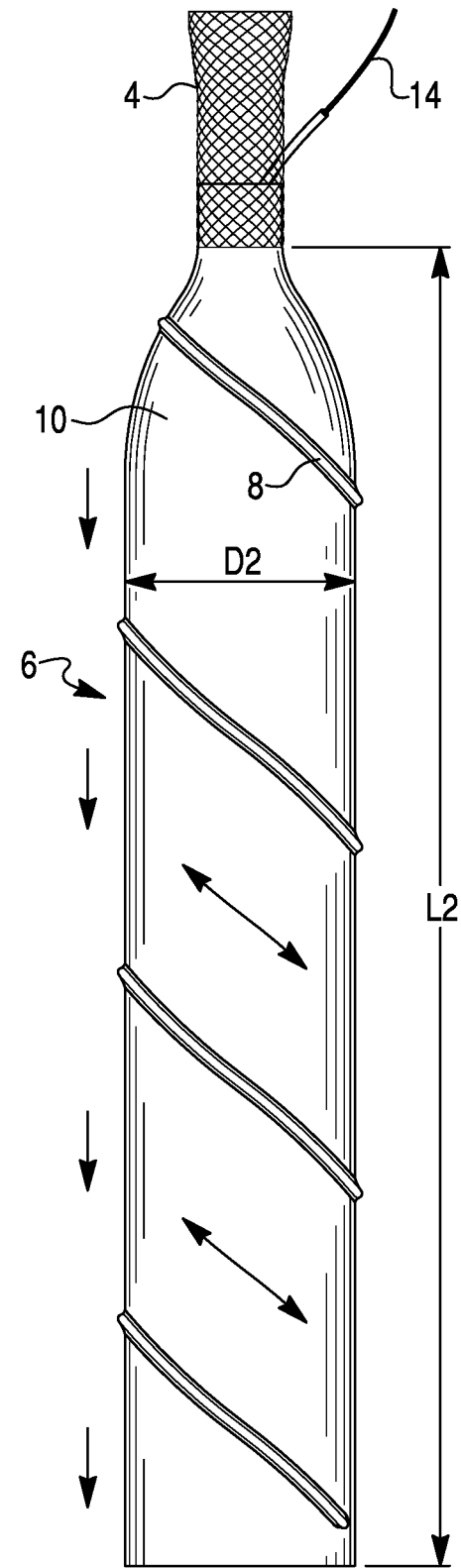

DEPLOYABLE SLEEVES AND RELATED METHODS

CROSS-REFERENCE TO RELATED APPLICATION(S)

This patent application claims the benefit under 35 U.S.C. § 119 to U.S. Provisional Patent Application No. 62/419,707, filed on Nov. 9, 2016, the entirety of which is incorporated herein by reference.

TECHNICAL FIELD

Examples of the present disclosure relate generally to medical devices for deploying in a lumen of a patient and related methods for deployment.

BACKGROUND

Medical devices that include sleeves may be deployed within a lumen of a patient for a variety of reasons. In some instances, sleeves are deployed within the gastrointestinal system (e.g., the intestines) to reduce absorption of nutrients. Sleeves also may be deployed after a bariatric procedure, such as a sleeve gastrectomy or a Roux-en-Y bypass, to protect a leak in a staple line or other damaged tissue area from food ingested by the patient. Sleeves have been used to treat gastroesophageal reflux disease (GERD) by implanting a stent within the esophagus with an attached sleeve extending into the patient's stomach. In other examples, sleeves are deployed in a patient's colon to protect a damaged area. In a variety of contexts, current sleeves may be made of a material that lacks rigidity and support, making them difficult to deploy within the desired body lumen. For example, the sleeve material may kink or bunch during attempted deployment.

SUMMARY

Embodiments of the present disclosure relate to, among other things, medical devices for deploying in a lumen of a patient and related methods for deployment. Each of the embodiments disclosed herein may include one or more of the features described in connection with any of the other disclosed embodiments.

In one example, a medical device may include a tubular sleeve configured for implantation in a body lumen, the sleeve having a first configuration with a first rigidity and a second configuration with a second rigidity greater than the first rigidity, the sleeve including: a flexible membrane defining an interior lumen; and a channel extending along the membrane.

The medical devices described herein may additionally or alternatively include one or more of the following features: the channel may be configured to receive and retain a fluid; the membrane may include a polymer; the medical device may further comprise an anchor coupled to a proximal end of the sleeve; the channel may include a self-sealing material, a valve, or a cap at a proximal end; the channel may be one of spiral-shaped or ring-shaped; the channel may include Nitinol; the medical device may further include an element secured to a distal end of the channel and extending through the channel to a proximal end of the channel, wherein applying a proximal force to the element is configured to at least one of axially shorten or radially shorten the sleeve, and releasing the proximal force is configured to at least one of axially lengthen or radially expand the sleeve; the channel may be defined by a material of the membrane; the channel may be radially outward of the membrane; the channel is not fluidly connected to the interior lumen; the channel may include perforations fluidly connecting the channel to an exterior of the sleeve; the channel may be configured to transform from the first configuration to the second configuration upon receipt of a fluid in the channel; the medical device may further comprise a second channel extending along the membrane; or the channel may include a closed distal end.

In another example, a medical device may include an anchor and a sleeve extending from the anchor, the sleeve including: a flexible membrane defining an interior lumen; and a channel configured to receive and retain a fluid.

The medical devices described herein may additionally or alternatively include one or more of the following features: the channel may be one of spiral-shaped or ring-shaped; the channel may be radially outward of the membrane; the channel is not fluidly connected to the interior lumen; the channel may include perforations fluidly connecting the channel to an exterior of the sleeve; or the channel may include a plurality of rings and a plurality of segments connecting the plurality of rings.

In yet another example, a method for implanting a medical device in a body lumen of a patient may include inserting a sleeve into the body lumen of the patient, the sleeve including a flexible membrane defining an interior lumen, and a channel; and injecting a fluid into the channel, the channel retaining the fluid.

The method may additionally or alternatively include one or more of the following features: injecting the fluid may include injecting the fluid through a self-sealing material or a valve at a proximal end of the channel; injecting the fluid may at least one of cause a diameter of the sleeve to increase or cause a length of the sleeve to increase; the method may further comprise using a vacuum source to remove at least some of the fluid from the channel; or injecting the fluid may cause a rigidity of the channel to increase.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIGS. 3A and 3B illustrate the ability of a sleeve to axially and radially expand, according to an exemplary embodiment.

DETAILED DESCRIPTION

The present disclosure is drawn to medical devices for deploying in a lumen of a patient and related methods for deployment. In general, the medical devices may include a sleeve having a channel or other structure that supports the sleeve during deployment and/or afterwards. The channel may have a modifiable rigidity to allow the sleeve to be less rigid in a first state and more rigid in a second state. In some examples, the channel may allow the sleeve to be radially expanded and/or contracted or axially expanded and/or contracted.

Figure 1A:
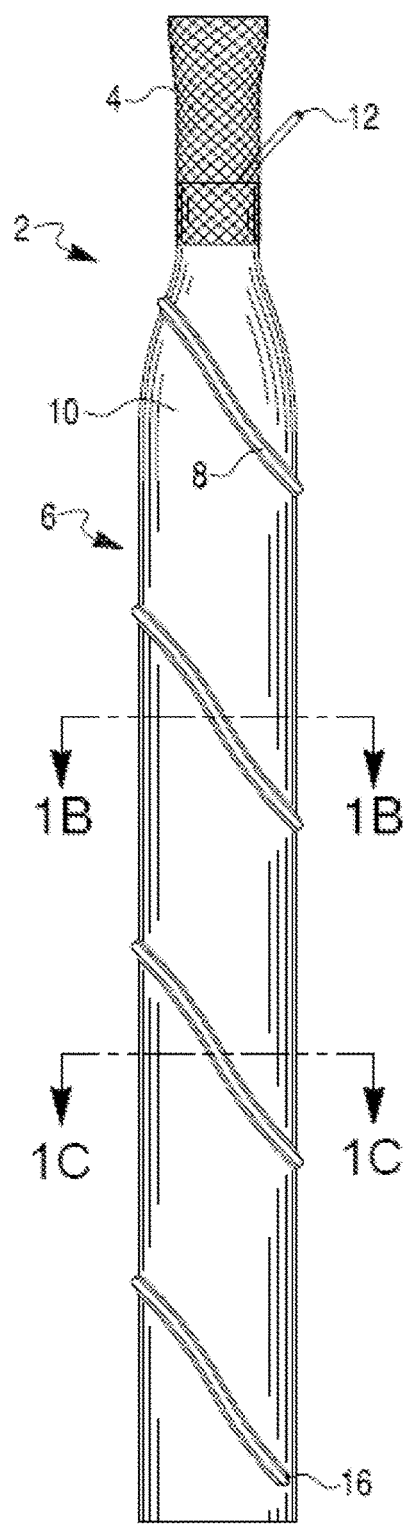
FIG. 1A illustrates a medical device that includes a sleeve according to an exemplary embodiment.

Referring to FIG. 1A, a medical device 2 may include a proximal anchor 4 and a distal sleeve 6. Sleeve 6 may include a support 8 and a membrane 10. In various examples, device 2 may have a length between 0.5-20 feet (0.15-6.1 meters), between 3-5 feet (0.9-1.5 meters), or about 2-4 feet (0.6-1.2 meters). However, the device may have a length of less than 0.5 feet (0.15 meters) or greater than 20 feet (6.1 meters). Sleeve 6 may be secured to a distal end of anchor 4. In one example, as shown in FIG. 1A, sleeve 6 extends partially into the lumen of anchor 4 and is secured by adhesive or other methods known in the art to anchor 4. In another example, membrane 10 may extend substantially, or all, of a length of device 2 and cover all other portions of device 2, including anchor 4. Membrane 10 may couple the sleeve 6 to the anchor 4.

Anchor 4 may be similar to a stent and may have a substantially cylindrical shape. Portions of anchor 4 may have different diameters than other portions. For example, a proximal portion of anchor 4 may have a larger diameter than a distal portion of anchor 4. In one example, anchor 4 may include a frame and a membrane covering the frame (e.g., a covered stent). In another example, anchor 4 may include a bare frame without a membrane (e.g., a bare stent). Anchor 4 may include a laser cut nitinol frame that resists elongation or does not elongate. Alternatively, anchor 4 may include a braided design. Anchor 4 may be self-expandable, like nitinol stents. In an alternative example, anchor 4 may be expanded by an expansion device, such as a balloon inserted within a lumen of anchor 4. Anchor 4 may include a one-way valve, such as an elastomeric slit valve or duck bill valve, to prevent retrograde flow of gastro-intestinal fluids.

Once implanted in a patient, anchor 4 may exert a radially outward force to help secure the device 2 to the body lumen. As described further below, anchor 4 may be positioned in the esophagus or the gastro-esophageal junction (GEJ) region, with sleeve 6 extending through the stomach or other portions of the gastro-intestinal system. In another example, anchor 4 may be positioned in the patient's intestine. In some examples, device 2 does not include anchor 4. Instead, sleeve 6 may be secured directly to the patient's tissue using sutures or any other suitable attachment mechanism.

Sleeve 6 may extend from the distal end of anchor 4 and may be have an elongated, tubular shape with an interior lumen. In one example, membrane 10 defines only one interior lumen. In an expanded configuration, sleeve 6 may be substantially cylindrical. Absent support 8, membrane 10 may be a flexible, thin membrane that readily collapses on itself. However, at certain times, as will be described below, support 8 may provide rigidity and structure to sleeve 6.

Membrane 10 may include one or more of the following polymer materials: polyethylene, polypropylene, polystyrene, polyester, biosorbable plastics (e.g., polylactic acid), polycarbonate, polyvinyl chloride, polyacrylate, acrylate, polysulfone, polyetheretherketone, thermoplastic elastomers, thermoset elastomers (e.g., silicone), poly-p-xylylene (parylene), flouropolymers (e.g., polytetrafluoroethylene (PTFE), polyvinylidene fluoride (PVDF), poly(vinylidene fluoride-co-hexafluoropropylene) (PVDF-HFP)), bioplastics (e.g., cellulose acetate). The sleeve may additionally or alternatively include one or more of: polyurethane and its copolymers, ethylene vinyl-acetate, polyethylene terephthalate (PET), polyolefins, cellulosics, polyam ides, acrylonitrile butadiene styrene copolymers, styrene isoprene butadiene (SIBS) block copolymers, acrylics, poly(glycolide-lactide) copolymer, Tecothane, PEBAX, poly(γ-caprolactone), poly(γ-hydroxybutyrate), polydioxanone, poly(γ-ethyl glutamate), polyiminocarbonates, poly(ortho ester), and/or polyanhydrides. Blends of the above polymers may also be employed.

Referring still to FIG. 1A, support 8 may form a spiral shape around membrane 10. Support 8 may include a channel having an interior lumen with an access point at a proximal end 12. The channel may have a closed distal end 16, such that fluid inserted into the proximal end 12 does not exit the channel through distal end 16. The channel may be separate from the interior lumen of sleeve 6 and in one example is not fluidly connected to the interior lumen of sleeve 6. Proximal end 12 may include a self-sealing material or membrane to allow the channel to be accessed by a needle. The needle may be connected to a syringe or other pump to allow fluid (e.g., air, liquid, saline, contrast medium) to be injected into the channel. Contrast medium may be injected into the channel to aid in visualization of sleeve 6 using fluoroscopy or other imaging methods. In another example, the proximal end 12 may include a valve or cap to allow access to the channel of support 8. After fluid has been injected into the channel, the channel may retain the fluid (e.g., via a self-sealing material, valve, or cap) until removal by a practitioner.

In one embodiment, support 8 extends around membrane 10 approximately four times. However, the spiral shape may be tighter (e.g., support 8 may extend around membrane 10 more than four times) or looser (e.g., support 8 may extend around membrane 10 less than four times) than the example shown in FIG. 1A. A tighter spiral may provide more support to sleeve 6, and a looser spiral may provide less support.

In various examples, support 8 may include different materials that provide different levels of rigidity. Support 8 may include a tubular channel defined by a metal (e.g., Nitinol) or a polymer. In some examples, the channel may be defined by the material of membrane 10 (e.g., a polymer). If the channel is defined by the material of membrane 10, it may have approximately the same rigidity as membrane 10. Accordingly, in an unfilled, first configuration, support 8 may be readily collapsible along with membrane 10. However, when support 8 is filled with fluid and expanded to a second configuration, support 8 may increase in rigidity to provide support to sleeve 6. The support 8, and therefore sleeve 6, may have different rigidities at different axial or radial locations. Variations in rigidity may be achieved by varying the diameter of the channel, the pitch of the spiral, or the material defining the channel. For example, in locations where the channel has a larger diameter (see FIG. 1C), the sleeve may be more rigid when the channel is filled than in locations where the channel has a smaller diameter (see FIG. 1B). In another example, a spiral having a smaller pitch may cause corresponding segments of sleeve 6 to be more rigid, while a spiral having a larger pitch may cause corresponding segments of sleeve 6 to be less rigid. In yet another example, a portion of the channel may be defined by a material having a higher rigidity (e.g., a metal) and a portion may be defined by a material having a lower rigidity (e.g., a flexible polymer).

Figure 1B:
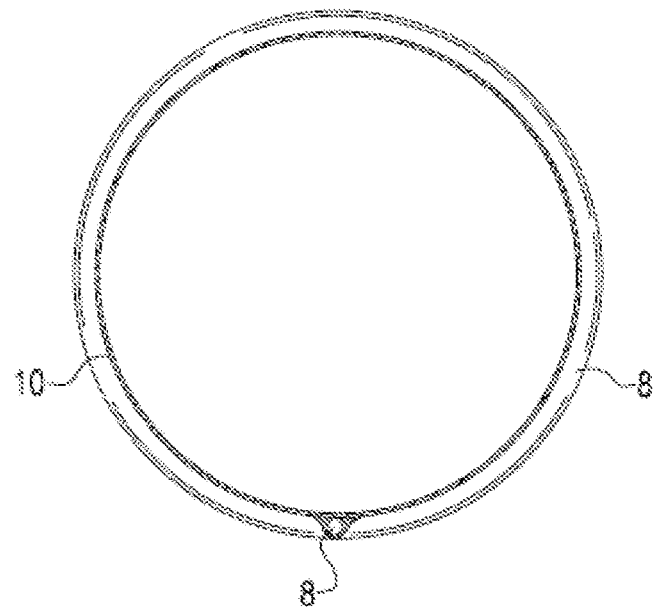
FIG. 1B illustrates a cross-sectional view of the sleeve of FIG. 1A, taken along line 1B-1B, according to an exemplary embodiment.
Figure 1C:
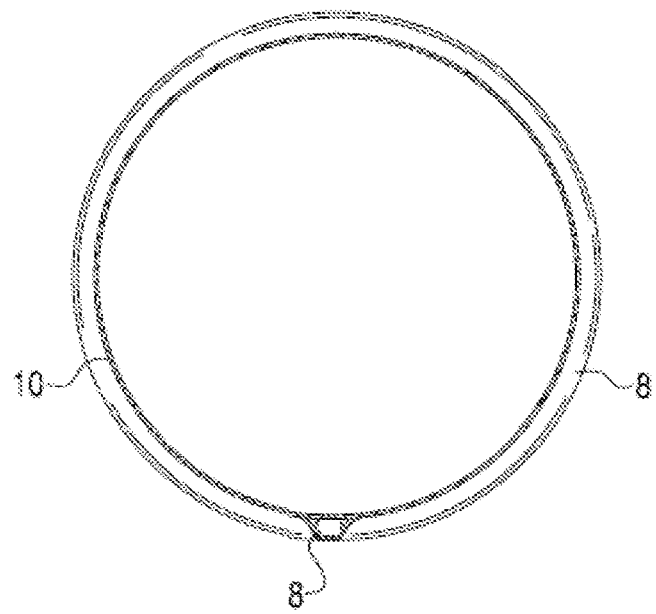
FIG. 1C illustrates a cross-sectional view of the sleeve of FIG. 1A, taken along line 1C-1C, according to an exemplary embodiment.

Support 8 may extend along a perimeter of sleeve 6. Support 8 may be positioned between two or more layers of material that form membrane 10 (e.g., an interior layer and an exterior layer), or otherwise embedded into the material that forms membrane 10. In other examples, support 8 may extend along the perimeter of sleeve 6 by being positioned proximate to membrane 10, either interior to membrane 10 or exterior to membrane 10. FIGS. 1B-1C illustrate support 8 positioned exterior to membrane 10. If support 8 is positioned interior or exterior to membrane 10, appropriate adhesives or other bonding methods may be used to secure support 8 to membrane 10, or support 8 and membrane 10 may be extruded or otherwise formed as an integral one-piece construction.

The support 8 may include perforations that connect the channel of support 8 to an exterior of sleeve 6. The perforations may allow drugs or other therapeutics to be delivered to the body lumen of the patient. The perforations may be evenly spaced along the length of sleeve 6 or may be clustered in select locations to target certain body portions. Exemplary therapeutics deliverable through perforations in support 8 include anti-inflammatories, antibiotics, antirestenosis (e.g., Paclitaxel, everolimus), cytotoxins, stem cells, anti-coagulants, or digestive enzyme aids.

In some examples, the sleeve 6 may include multiple supports 8. Each support 8 may be spiral-shaped. The multiple supports may extend parallel to each other along the length of sleeve 6, or may extend in opposite directions such that the multiple spirals intersect with each other at various points along the length of sleeve 6. Each support 8 may serve the same or different purposes as the other supports 8. For example, one or more supports 8 may be configured to be filled with a substance to provide the sleeve with additional rigidity, one or more supports 8 may be used for drug delivery, and one or more supports 8 may be filled with contrast medium.

Support 8 may include other configurations besides a spiral. For example, support 8 may include a plurality of rings around sleeve 6 connected by a plurality of segments extending parallel to the longitudinal axis of sleeve 6. If the support 8 includes channels, the various rings and segments of support 8 may be connected by a continuous lumen that allows inflation and deflation from a single proximal access point.

Figure 2A:
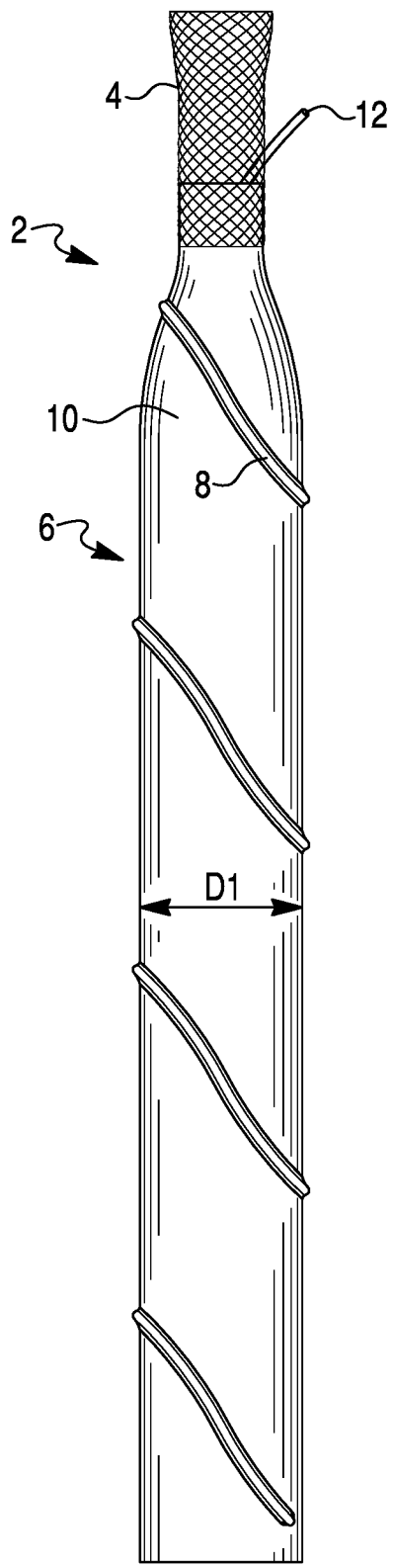
FIGS. 2A and 2B illustrate the ability of a sleeve to radially expand, according to an exemplary embodiment.
Figure 2B:
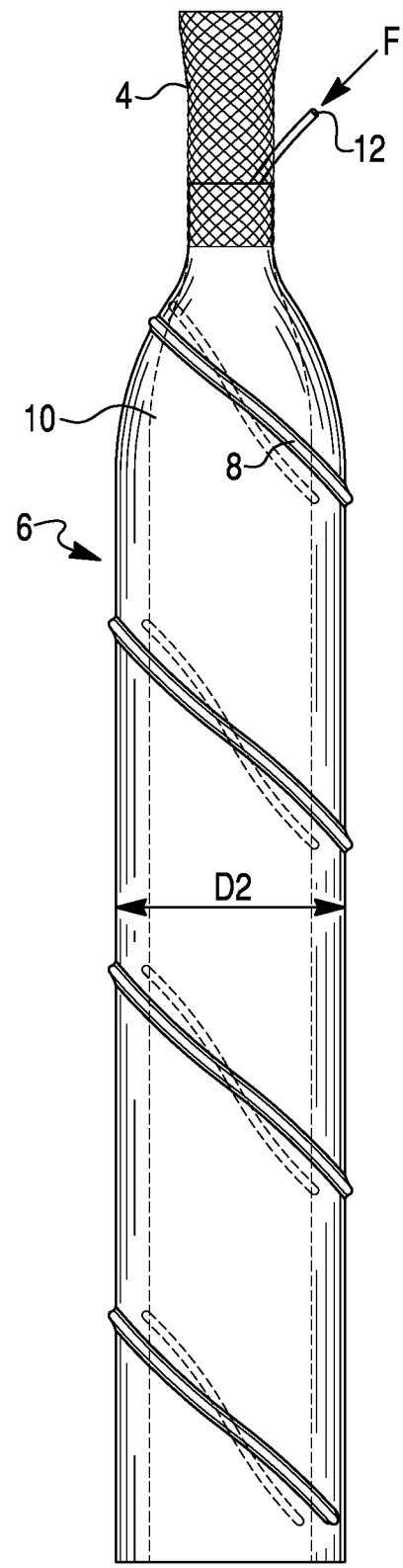

FIGS. 2A and 2B illustrate the use of support 8 to radially expand sleeve 6. In FIG. 2A, support 8 is unfilled and in a first configuration, and sleeve 6 has a first diameter D1 and a first rigidity. Fluid F (e.g., air, liquid, saline, contrast medium) may be injected into the proximal end 12 of support 8. The injected fluid may cause support 8 to increase in rigidity to a second rigidity greater than the first rigidity, which may cause the channel itself to expand (not shown) and/or may cause the sleeve 6 to radially expand. The expanded sleeve 6 is shown in FIG. 2B and has a diameter D2, in which D2 is larger than D1. In some examples, sleeve 6 may also increase in length when fluid is injected into support 8, as will be described in connection with FIGS. 3A and 3B. In other examples, injecting fluid into support 8 may increase the rigidity of support 8 without causing sleeve 6 to change in diameter or length. The rigidity of support 8 and accordingly the radial and/or axial expansion of sleeve 6 may be controlled by the amount of fluid that is injected into support 8. Injecting a small amount of fluid may cause a corresponding small increase in rigidity of support 8 and/or expansion of sleeve 6. Similarly, injecting a large amount of fluid may cause a correspondingly large increase in rigidity of support 8 and/or expansion of sleeve 6. After injection, the channel may retain the fluid until a practitioner desires to remove the fluid from the channel, e.g., through aspiration applied at proximal end 12.

FIGS. 3A and 3B illustrate the use of support 8 to both axially and radially constrict and expand sleeve 6. Support 8 may include a channel with an elongated element, such as suture 14, extending through the channel. The suture 14 may be secured to a distal end of the interior of the channel, e.g., via any suitable adhesive or method of securement. To obtain the first, contracted configuration shown in FIG. 3A, a force may be applied to suture 14 in a proximal direction to contract sleeve 6 axially along its longitudinal axis to a length L1. The pulling of suture 14 may further cause support 8, and therefore sleeve 6, to contract in a radial direction to a diameter D1. The support 8 may include a shape memory material, such as Nitinol, along all or a portion of its length. Accordingly, when the suture 14 is released, the support 8 may be biased to self-expand to the second, expanded configuration shown in FIG. 3B. In the second configuration, support 8 has caused sleeve 6 to expand both in an axial direction to length L2 and in a radial direction to diameter D2. In an alternative example to that shown in FIGS. 3A and 3B, the suture is eliminated and the support does not include a shape memory material. Instead, the channel of support 8 of FIG. 3A may be filled with a fluid, as described in connection with FIGS. 2A and 2B, to cause the axial and radial expansion of sleeve 6 shown in FIG. 3B.

Once implanted, the fluid may remain in the channel of support 8 to provide continued support to sleeve 6. In another example, support 8 may be inflated further to increase rigidity or deflated (e.g., by removing fluid) to allow sleeve 6 to revert to a less rigid, structured configuration that places little to no force on adjacent tissue. The rigidity of support 8 may be decreased by applying a vacuum source to the proximal end 12 of support 8. An intermediate fill level, achieved by either not inflating support 8 to a maximum amount or by removing some fluid from a fully-inflated support 8, may provide some structural support but still cause sleeve 6 to exert less outward force on adjacent tissue than a stent. Continued application of a vacuum to remove fluid from support 8 may cause sleeve 6 to contract in diameter and/or length, and/or to assume an unstructured, more floppy configuration. In other examples (e.g., if support 8 includes Nitinol or another rigid material), support 8 may be restricted (e.g., by pulling suture 14) after the initial implantation to achieve a shortened length and/or diameter of sleeve 6.

Support 8 may allow for size adjustment for patients having different sized anatomies. For example, for patients having a smaller body lumen (e.g., intestine), support 8 may be filled only partially to expand sleeve 6. For patients with a larger body lumen, support 8 may be filled to a greater degree to cause sleeve 6 to expand to a wider diameter. Similarly, if support 8 includes a suture 14, the suture 14 may be adjusted to lengthen or shorten sleeve 6 or to increase or decrease its diameter. Post-implantation (e.g., days weeks, or months later), support 8 may similarly allow for adjustments in the size of sleeve 6 to achieve different objectives. For example, for obesity treatment, sleeve 6 may be lengthened or shortened to prevent or allow, respectively, certain digestive juices from reacting with food or to reduce or increase, respectively, the absorption of food.

Sleeve 6 may be used in a variety of contexts. In one use, sleeve 6 may be used to treat obesity. For example, sleeve 6 may be implanted into the patient's intestines to reduce absorption of nutrients, with or without an anchor 4 to help secure sleeve 6. Anchor 4 may be positioned near or at the pylorus, with the sleeve 6 extending into the patient's intestines. Alternatively, anchor 4 may be positioned in the patient's GEJ region, with sleeve 6 extending though the stomach and into the patient's intestines. The ability to modify the length of sleeve 6 may be useful to adjust the level of nutrient absorption. For example, shortening sleeve 6 may allow the patient to absorb more nutrients, whereas lengthening sleeve 6 may further reduce nutrient absorption.

In another example, sleeve 6 may be implanted after a bariatric procedure. Patients who undergo a sleeve gastrectomy or Roux-en-Y procedure, for example, may develop leaks, infections, or other complications post-surgery. Anchor 4 may be positioned in an esophagus or in the GEJ region of the patient, and sleeve 6 may extend through a stomach sleeve formed during the sleeve gastrectomy procedure or through a limb created during the Roux-en-Y procedure to protect the injured area. In yet another example, sleeve 6 may be used to protect the patient's colon after colon surgery. Anchor 4 may be deployed proximal to the injured area, and sleeve 6 may extend over the injured tissue.

One currently-existing solution to protect injured portions of body lumens is to position a covered stent within the lumen and over the injured area, but stents may be traumatic to the weakened tissue. Placement of a sleeve, in contrast, may protect the injured area and allow food and other substances to bypass the injured area, without exerting unnecessary outward pressure on the injured tissue. Currently-existing sleeves, however, can be difficult to deploy and can wrinkle or bunch. In contrast, support 8 of sleeve 6 described herein may allow successful deployment by preventing sleeve 6 from wrinkling or bunching during deployment or afterwards, while exerting less outward force than a stent.

In another example, sleeve 6 may be used to treat gastroesophageal reflux disease. Anchor 4 may be positioned in the patient's esophagus or the GEJ region, and sleeve 6 may extend into the patient's stomach. Support 8 may be inflated during implantation to aid in correct positioning of sleeve 6. After implantation, the fluid may be removed from support 8 so that the membrane 10 resumes a less rigid, unstructured configuration in which it can collapse onto itself. The membrane prevents reflux of stomach contents by collapsing onto itself but allows food to flow through sleeve 6 in a proximal-to-distal direction.

Sleeve 6 may be delivered to a patient using standard delivery methods. For example, sleeve 6 may be inserted into a delivery catheter and placed transorally or transrectally into the patient's gastrointestinal system. As described herein, once inside the patient, fluid (e.g., air, liquid, saline, or contrast medium) may be inserted into a channel of support 8 to increase the rigidity of support 8. In other embodiments, a restraint, such as a suture, may be released to allow support 8 to self-expand. The increased rigidity of support 8 and/or the self-expansion of support 8 may cause sleeve 6 to deploy more effectively that currently-existing sleeves. Sleeve 6 may be removed from the patient by removing any fluid from support 8 (if the fluid was not removed previously) and/or constricting support 8 using a suture or other method (e.g., physically constricting the sleeve within a tube). Sleeve 6 may then be pulled transorally or transrectally from the patient.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A medical device, comprising:
    a tubular sleeve having a proximal end configured for fixing to a body lumen, the tubular sleeve having a first configuration with a first rigidity and a first length, and a second configuration with a second rigidity greater than the first rigidity and a second length greater than the first length;
    wherein the tubular sleeve is configured to expand from the first length to the second length in a single direction away from the proximal end when the proximal end is fixed to the body lumen, the tubular sleeve including:
        a flexible membrane defining an interior lumen; and
        a support member comprising a channel extending along the flexible membrane and including a plurality of perforations grouped together in a cluster at a location on the channel, the plurality of perforations fluidly connecting the channel to an exterior of the tubular sleeve and configured to target a portion of the body lumen positioned in alignment with the cluster along the flexible membrane, the channel having a diameter that increases from a proximalmost end of the channel to a distalmost end of the channel such that the flexible membrane has a rigidity that increases from the proximalmost end to the distalmost end.

2. The medical device of claim 1, the channel being configured to receive a fluid for delivery to the portion of the body lumen via the plurality of perforations.

3. The medical device of claim 1, wherein the flexible membrane includes a polymer.

4. The medical device of claim 1, further comprising an anchor coupled to the proximal end of the tubular sleeve, wherein the anchor is fixed to the body lumen such that a distal end of the tubular sleeve is configured to move away from the proximal end when the tubular sleeve transitions from the first configuration to the second configuration.

5. The medical device of claim 1, wherein the channel includes a self-sealing material, a valve, or a cap at the proximalmost end.

6. The medical device of claim 1, wherein the channel is one of spiral-shaped or ring-shaped.

7. The medical device of claim 1, further comprising an element secured to the distalmost end of the channel and extending through the channel to the proximalmost end of the channel, wherein applying a proximal force to the element is configured to at least one of axially shorten or radially shorten the tubular sleeve, and releasing the proximal force is configured to at least one of axially lengthen or radially expand the tubular sleeve.

8. The medical device of claim 1, wherein the channel is embedded into a material of the flexible membrane such that the channel is flush with an exterior surface of the flexible membrane.

9. A medical device, comprising:

a sleeve having a first configuration with a first rigidity and a first length, and a second configuration with a second rigidity greater than the first rigidity and a second length greater than the first length, the sleeve moving from the first configuration to the second configuration upon fixing at least one end of the sleeve body to a body lumen;

the sleeve including:
- a membrane defining an interior lumen; and
- a support member comprising a channel extending along the membrane, the channel having a diameter that increases from a proximalmost end to a distalmost end of the channel, the channel is formed of a shape-memory material that is configured to bias the sleeve to move from the first configuration to the second configuration, wherein the channel is configured to increase a rigidity of the membrane from the proximalmost end to the distalmost end.

10. The medical device of claim 9, wherein the channel includes a self-sealing material or a valve at the proximalmost end.

11. The medical device of claim 9, wherein the channel is embedded into the membrane such that the channel is flush with an exterior surface of the membrane.

12. The medical device of claim 9, wherein the channel includes at least one perforation positioned along the membrane.

13. The medical device of claim 12, wherein the sleeve is configured to deliver a fluid through the channel and to a body lumen via the at least one perforation.

14. The medical device of claim 9, wherein the sleeve includes a first diameter when in the first configuration, and a second diameter that is greater than the first diameter when in the second configuration, such that the sleeve is configured to increase in length, rigidity, and diameter when moving from the first configuration to the second configuration.

\* \* \* \* \*